(12) United States Patent
Lorenzo

(10) Patent No.: US 9,693,885 B2
(45) Date of Patent: *Jul. 4, 2017

(54) RADIOPAQUE MARKERS FOR IMPLANTABLE STENTS AND METHODS FOR MANUFACTURING THE SAME

(71) Applicant: Codman & Shurtleff, Inc., Raynham, MA (US)

(72) Inventor: Juan A. Lorenzo, Raynham, MA (US)

(73) Assignee: Depuy Synthes Products, Inc., Raynham, MA (US)

(*) Notice: Subject to any disclaimer, the term of this patent is extended or adjusted under 35 U.S.C. 154(b) by 892 days.

This patent is subject to a terminal disclaimer.

(21) Appl. No.: 13/739,269

(22) Filed: Jan. 11, 2013

(65) Prior Publication Data

US 2013/0131785 A1  May 23, 2013

Related U.S. Application Data

(62) Division of application No. 11/694,580, filed on Mar. 30, 2007, now Pat. No. 8,545,548.

(51) Int. Cl.
*A61F 2/86* (2013.01)
*A61F 2/82* (2013.01)
*A61F 2/91* (2013.01)
*A61F 2/915* (2013.01)
*A61B 90/00* (2016.01)

(52) U.S. Cl.
CPC ............... *A61F 2/82* (2013.01); *A61F 2/91* (2013.01); *A61B 2090/3966* (2016.02); *A61F 2/86* (2013.01); *A61F 2/915* (2013.01); *A61F 2220/0041* (2013.01); *A61F 2220/0058* (2013.01); *A61F 2230/0013* (2013.01);
(Continued)

(58) Field of Classification Search
CPC combination set(s) only.
See application file for complete search history.

(56) References Cited

U.S. PATENT DOCUMENTS 4,041,931 A    8/1977   Elliott
4,579,594 A    4/1986   Nanao et al.
(Continued)

FOREIGN PATENT DOCUMENTS

EP    634546 A2    1/1995
EP    634546 A3    1/1995
(Continued)

OTHER PUBLICATIONS

European Search Report in EP 08251090.0, dated Jun. 20, 2008.
(Continued)

*Primary Examiner* — Thomas J Sweet
*Assistant Examiner* — Cheryl Miller
(74) *Attorney, Agent, or Firm* — Cook Alex Ltd.

(57) ABSTRACT

Radiopaque markers for use with stents implantable within a body vessel are provided with one or more through-holes. Each through-hole extends through the thickness of the marker to expose a portion of the stent underlying the marker. The marker is welded to the stent through each through-hole. Also provided are stents incorporating a radiopaque marker having one or more through-holes suitable for receiving a plug weld. Methods are provided for securing a radiopaque marker having one or more through-holes to a stent via welds.

9 Claims, 2 Drawing Sheets

(52) U.S. Cl.
CPC ............... *A61F 2230/0043* (2013.01); *A61F 2250/0098* (2013.01)

(56) References Cited

U.S. PATENT DOCUMENTS

| | | | |
|---|---|---|---|
| 4,668,299 | A | 5/1987 | Nanao et al. |
| 5,370,691 | A | 12/1994 | Samson |
| 5,393,164 | A | 2/1995 | Renner et al. |
| 5,458,629 | A | 10/1995 | Baudino |
| 5,643,278 | A | 7/1997 | Wijay |
| 5,649,978 | A | 7/1997 | Samson |
| 5,662,622 | A | 9/1997 | Gore |
| 5,669,932 | A | 9/1997 | Fischell |
| 5,718,724 | A | 2/1998 | Goicoechea |
| 5,741,327 | A | 4/1998 | Frantzen |
| 5,916,263 | A | 6/1999 | Goicoechea |
| 5,938,696 | A | 8/1999 | Goicoechea |
| 5,972,019 | A | 10/1999 | Engelson |
| 6,022,374 | A | 2/2000 | Imran |
| 6,051,020 | A | 4/2000 | Goicoechea |
| 6,117,167 | A | 9/2000 | Goicoechea |
| 6,203,568 | B1 | 3/2001 | Lombardi |
| 6,264,671 | B1 | 7/2001 | Stack |
| 6,277,108 | B1 | 8/2001 | McBroom |
| 6,293,966 | B1 | 9/2001 | Frantzen |
| 6,302,906 | B1 | 10/2001 | Goicoechea |
| 6,315,790 | B1 | 11/2001 | Gerberding |
| 6,331,189 | B1 | 12/2001 | Wolinsky |
| 6,334,871 | B1 | 1/2002 | Dor et al. |
| 6,340,367 | B1 | 1/2002 | Stinson |
| 6,391,044 | B1 | 5/2002 | Yadav |
| 6,402,777 | B1 | 6/2002 | Globerman et al. |
| 6,464,723 | B1 | 10/2002 | Callol |
| 6,471,721 | B1 | 10/2002 | Dang |
| 6,520,984 | B1 | 2/2003 | Garrison |
| 6,554,848 | B2 | 4/2003 | Boylan |
| 6,554,854 | B1 | 4/2003 | Flanagan |
| 6,585,757 | B1 | 7/2003 | Callol |
| 6,612,012 | B2 | 9/2003 | Mitelberg |
| 6,623,520 | B2 | 9/2003 | Jalisi |
| 6,626,936 | B2 | 9/2003 | Stinson |
| 6,673,106 | B2 | 1/2004 | Mitelberg |
| 6,818,013 | B2 | 11/2004 | Mitelberg |
| 6,833,003 | B2 | 12/2004 | Jones |
| 6,899,914 | B2 | 5/2005 | Schmitz |
| 6,918,928 | B2 | 7/2005 | Wolinsky |
| 6,955,685 | B2 | 10/2005 | Escamilla |
| 6,960,227 | B2 | 11/2005 | Jones |
| 6,970,734 | B2 | 11/2005 | Eidenschink |
| 7,001,422 | B2 | 2/2006 | Escamilla |
| 7,037,331 | B2 | 5/2006 | Mitelberg |
| 7,208,008 | B2 | 4/2007 | Clarke |
| 7,267,685 | B2 | 9/2007 | Butaric et al. |
| 7,291,167 | B2 | 11/2007 | DiCaprio |
| 7,344,559 | B2 | 3/2008 | Gray et al. |
| 7,462,190 | B2 | 12/2008 | Lombardi |
| 7,480,973 | B2 | 1/2009 | Miller |
| 7,641,647 | B2 | 1/2010 | Gunderson |
| 7,761,138 | B2 | 7/2010 | Wang |
| RE42,244 | E | 3/2011 | Boatman |
| 7,913,371 | B2 | 3/2011 | Klocke et al. |
| 7,985,213 | B2 | 7/2011 | Parker |
| 8,021,418 | B2 | 9/2011 | Gerberding |
| 8,322,593 | B2* | 12/2012 | Wack ............... A61F 2/915 228/170 |
| 8,475,520 | B2* | 7/2013 | Wack ............... A61F 2/915 623/1.34 |
| 8,545,548 | B2* | 10/2013 | Lorenzo ............ A61F 2/91 623/1.34 |
| 8,739,382 | B2* | 6/2014 | Sheldon ............ A61F 2/90 29/439 |
| 9,044,351 | B2* | 6/2015 | Wang ............... A61F 2/91 |
| 2001/0021873 | A1 | 9/2001 | Stinson |
| 2002/0095205 | A1 | 7/2002 | Edwin |
| 2003/0023299 | A1 | 1/2003 | Amplatz et al. |
| 2003/0055493 | A1 | 3/2003 | Carpenter |
| 2003/0144725 | A1 | 7/2003 | Lombardi |
| 2003/0225448 | A1 | 12/2003 | Gerberding |
| 2004/0015229 | A1 | 1/2004 | Fulkerson |
| 2004/0044399 | A1 | 3/2004 | Ventura |
| 2004/0073291 | A1 | 4/2004 | Brown et al. |
| 2004/0167619 | A1 | 8/2004 | Case et al. |
| 2004/0254637 | A1 | 12/2004 | Yang et al. |
| 2004/0254639 | A1 | 12/2004 | Li |
| 2005/0049670 | A1 | 3/2005 | Jones |
| 2005/0064224 | A1 | 3/2005 | Bavaro |
| 2005/0113686 | A1 | 5/2005 | Peckham |
| 2005/0148866 | A1 | 7/2005 | Gunderson |
| 2005/0209678 | A1* | 9/2005 | Henkes ............ A61B 17/12118 623/1.12 |
| 2005/0234536 | A1 | 10/2005 | Mitelberg |
| 2005/0240257 | A1 | 10/2005 | Ishimaru |
| 2006/0015173 | A1 | 1/2006 | Clifford |
| 2006/0258982 | A1* | 11/2006 | Powell ............ A61M 25/001 604/103.1 |
| 2007/0055359 | A1 | 3/2007 | Messer |
| 2007/0156230 | A1 | 7/2007 | Dugan et al. |
| 2008/0009938 | A1 | 1/2008 | Huang et al. |
| 2008/0228170 | A1 | 9/2008 | Murray |
| 2008/0243227 | A1 | 10/2008 | Lorenzo |
| 2008/0288046 | A1 | 11/2008 | Hemerick |
| 2009/0076594 | A1 | 3/2009 | Sabaria |
| 2009/0326637 | A1 | 12/2009 | Hashimoto |
| 2010/0234935 | A1 | 9/2010 | Bashiri |
| 2012/0095546 | A1 | 4/2012 | Yokoi |
| 2012/0330401 | A1 | 12/2012 | Sugimoto et al. |
| 2013/0131785 | A1 | 5/2013 | Lorenzo |

FOREIGN PATENT DOCUMENTS

| | | |
|---|---|---|
| EP | 1 488 763 A2 | 12/2004 |
| EP | 1488763 A2 | 12/2004 |
| EP | 1488763 A3 | 12/2004 |
| EP | 1 634 546 A1 | 3/2006 |
| EP | 1634546 A1 | 3/2006 |
| EP | 1 488 763 B1 | 11/2007 |
| EP | 634 546 B1 | 11/2007 |
| WO | WO 01/58384 A1 | 8/2001 |
| WO | WO 0158384 | 8/2001 |

OTHER PUBLICATIONS

Excerpt from mig-welding.co.uk with comment of Jun. 29, 2011 on pictures of welds.
Welded connections excerpt at Mitcale.com, downloaded Dec. 6, 2012.
Excerpt from esabna.com, Plug Weld Joining Two plates, downloaded Dec. 6, 2012.
European Search Report in DePuy Synthes EP 14158492.0, dated Jun. 25, 2004.
German Patent Publication No. DE 10 2011 015995, Buechart, Acandis GmbH & Co. KG, dated Oct. 4, 2012, with English abstract.
Navigate Tough Anatomy; brochure Copyright 2009; Codman & Shurtleff, Inc., 325 Paramount Drive, Raynham, Massachusetts.
MIG-Welding.CO.UK; Excerpt from with comment of Jun. 29, 2011 on pictures of welds.
Mitcale.com; Welded connections excerpt, downloaded Dec. 6, 2012.
Plug Weld Joining Two Plates; Excerpt from esabna,com, downloaded Dec. 6, 2012.
Navigate Tough Anatomy; brochure Copyright 2009; Cadman & Shurtleff, Inc., 325 Paramount Drive, Raynham, Massachusetts.
Non-Final Rejection U.S. Appl. No. 11/694,580 dated Sep. 26, 2012.
Non-Final Rejection U.S. Appl. No. 11/694,580 dated Oct. 28, 2010.
Non-Final Rejection U.S. Appl. No. 11/694,580 dated May 12, 2010.
Non-Final Rejection U.S. Appl. No. 11/694,580 dated May 19, 2009.

(56) References Cited

OTHER PUBLICATIONS

Non-Final Rejection U.S. Appl. No. 11/694,580 dated Aug. 20, 2008.
Final Rejection U.S. Appl. No. 11/694,580 dated Mar. 22, 2011.
Final Rejection U.S. Appl. No. 11/694,580 dated Oct. 5, 2009.
Final Rejection U.S. Appl. No. 11/694,580 dated Feb. 9, 2009.

\* cited by examiner

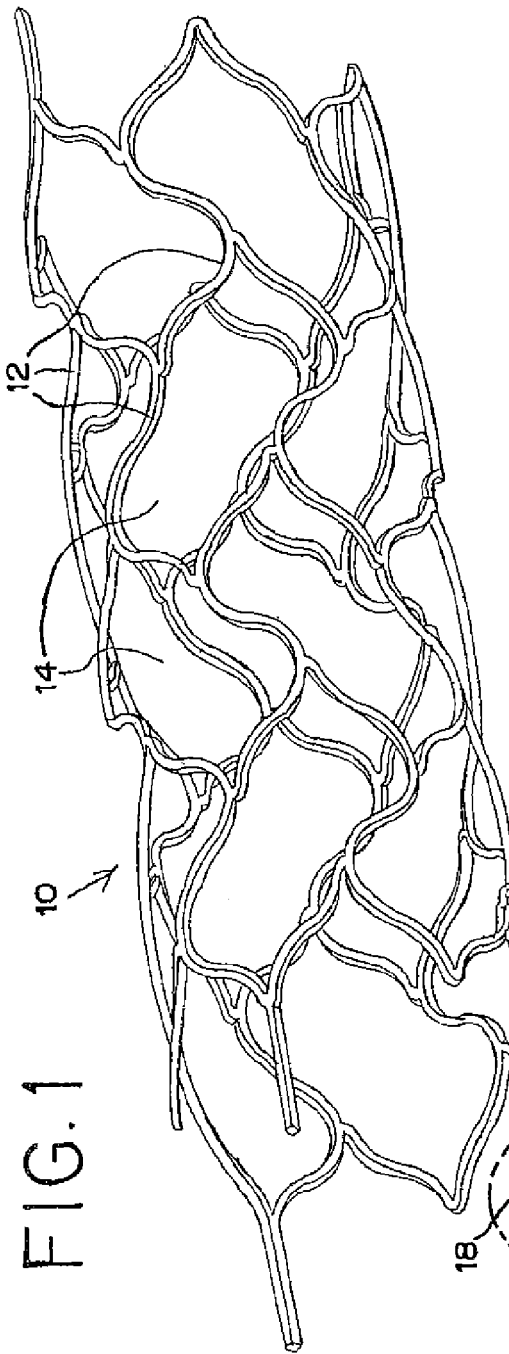
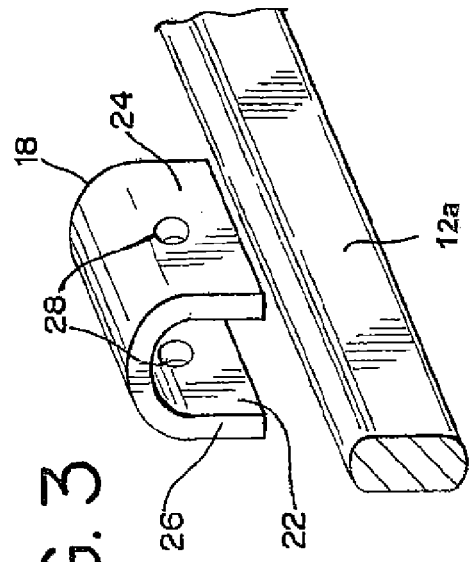
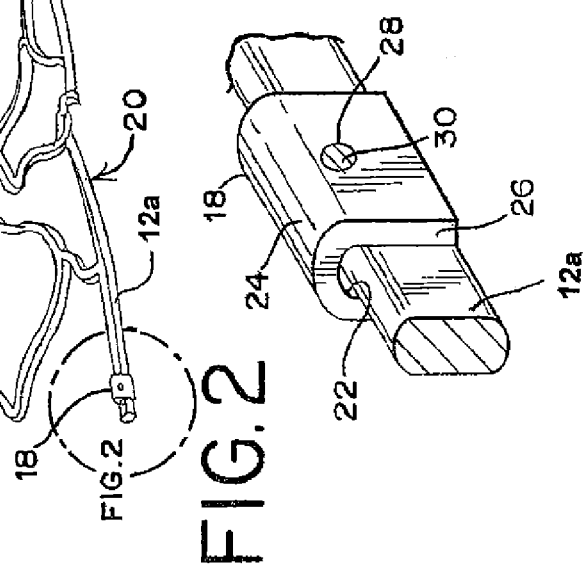

RADIOPAQUE MARKERS FOR IMPLANTABLE STENTS AND METHODS FOR MANUFACTURING THE SAME

This is a divisional of U.S. patent application Ser. No. 11/694,580, filed Mar. 30, 2007, now U.S. Pat. No. 8,545,548 hereby incorporated by reference hereunto.

FIELD OF THE INVENTION

This invention relates to intravascular devices for implantation within a vessel of the body, and more particularly to a stent device which may be used in the treatment of blood vessel disorders. More particularly, this invention relates to stent devices having at least one radiopaque marker and methods for making the same.

DESCRIPTION OF RELATED ART

Medical devices that can benefit from the present invention include those that are characterized by hollow interiors and that are introduced endoluminally and expand when deployed. These are devices that move or are moved between collapsed and expanded conditions or configurations for ease of deployment through catheters and introducers. Such devices are typically introduced to a diseased location within a body vessel (e.g., a stenosed section or an aneurysm) and may perform a variety of functions, including support and/or occlusion.

Endoluminal stents typically have a relatively open structure, with a plurality of interconnecting struts which define pores or openings in and/or through the surface that can allow for endothelialization and more permanent fixture of the stent within the vessel after implantation. Certain stents have an especially open structure in order to allow blood flow through the openings and to peripheral arteries after implantation of the stent adjacent to an aneurysm. Typically, the pores or openings are added by masking and/or etching techniques or laser- or water-jet cutting. Known stents include the Cordis Enterprise® line of self-expanding stents, which are described in numerous patents and published patent applications, including U.S. Pat. Nos. 6,612,012; 6,673,106; 6,818,013; 6,833,003; 6,955,685; 6,960,227; 7,001,422; and 7,037,331 and U.S. Patent Application Publication No. 2005/0234536, all of which are hereby incorporated by reference hereinto.

Stents have been developed with radiopaque markers to aid in the initial positioning of the stent within a body vessel and for visualization of the stent after deployment. Radiopaque markers facilitate the positioning of the stent within a blood vessel by allowing a physician to determine the exact location, size, and orientation of the stent under x-ray or fluoroscopy. These markers are typically formed of a radiopaque material such as tantalum, zirconium, gold, or platinum. U.S. Pat. No. 6,955,685 describes one known marking technique and is hereby incorporated by reference hereinto. This marking technique involves forming a stent strut with a portion having a plurality of threads. A coil of radiopaque material is wound around the threads and held in place by a UV adhesive.

One potential drawback of known marking techniques is their cost and complexity. For example, in techniques according to the foregoing description, the strut must be specially formed to include a threaded portion. Further, marker coils are very small, typically having a diameter on the order of 0.008 inch and a length on the order of one millimeter, so it may be difficult to manufacture and handle them or to properly wind them onto a threaded portion. These problems are further exacerbated by the fact that stents typically include a plurality of markers, so any manufacturing inefficiencies are multiplied.

Accordingly, a general aspect or object of the present invention is to provide an improved stent marking system that allows for increased manufacturing and assembly efficiency.

Other aspects, objects and advantages of the present invention, including the various features used in various combinations, will be understood from the following description according to preferred embodiments of the present invention, taken in conjunction with the drawings in which certain specific features are shown.

SUMMARY

In accordance with an aspect of the present invention, a radiopaque marker is provided. The radiopaque marker is securable to a strut of a stent implantable within a body vessel of a human subject and comprises an inner surface. The inner surface of the marker is adapted for engagement with a strut of a stent. The marker further includes an outer surface and a thickness separating the inner surface from the outer surface. At least one through-hole passes through the thickness, allowing for access to a portion of a strut underlying the radiopaque marker when the inner surface is engaged against a strut. The through-hole is adapted for at least partially receiving a weld to secure the radiopaque marker to a strut.

In accordance with another aspect of the present invention, a stent implantable within a body vessel comprises a strut with a receiving surface, a first projection at a first end of the receiving surface, and a second projection at a second end of the receiving surface. A radiopaque marker is received between the first projection and the second projection. The radiopaque marker comprises an inner surface engaging at least a portion of the receiving surface, an outer surface, and a thickness separating the inner surface from the outer surface. At least one through-hole passes through the thickness and allows for access to a portion of the receiving surface underlying the radiopaque marker. A weld is at least partially received by the through-hole to secure the radiopaque marker to the strut.

In accordance with yet another aspect of the present invention, a method of securing a radiopaque marker to a stent implantable within a body vessel includes providing a stent having a strut. A radiopaque marker is provided. The radiopaque marker comprises an inner surface, an outer surface, a thickness separating the inner surface from the outer surface, and at least one through-hole passing through the thickness. The inner surface is positioned against the strut such that the through-hole allows for access to a portion of the strut underlying the radiopaque marker. Thereafter, the radiopaque marker is welded to the strut through the through-hole.

BRIEF DESCRIPTION OF THE DRAWINGS

FIG. 1 is a perspective view of a stent according to an aspect or embodiment of the present invention;

FIG. 2 is a detail view of a strut and radiopaque marker illustrated in FIG. 1;

FIG. 3 is an exploded view of the strut and radiopaque marker of FIG. 2;

DESCRIPTION OF ILLUSTRATED EMBODIMENTS

Figure 4:
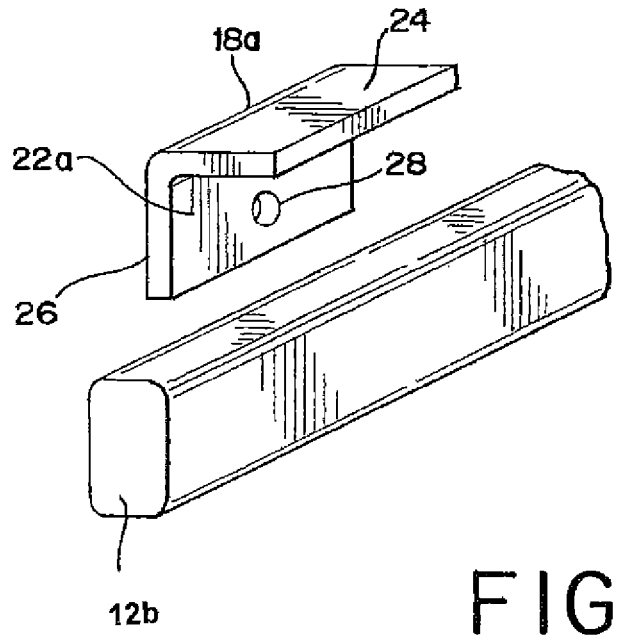
FIG. 4 is a perspective view of a strut and another radiopaque marker according to an aspect of the present invention.

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 shows a stent 10 which is implantable within a body vessel. The illustrated stent 10 is a substantially tubular device comprised of a plurality of interconnecting struts 12, 12a. The struts 12, 12a may be formed by any of a number of methods including, but not limited to, laser cutting, water jet cutting, and etching. The struts 12, 12a define a plurality of cells 14, which are deformable to allow the stent 10 to move between a small-diameter "compressed" or "delivery" condition (typically during manufacture and delivery) and a large-diameter "expanded" or "deployed" condition (during deployment and, in some cases, manufacture). A closed-cell configuration is shown in FIG. 1, but an open-cell configuration may also be employed without departing from the scope of the present invention. Stents according to the present invention may be self-expanding or balloon-expandable or partially self-expanding and partially balloon-expandable.

One strut 12a is illustrated with a radiopaque marker 18 according to the present invention. The strut 12a is shown at a proximal end 20 of the stent 10, but it will appreciated that radiopaque markers according to the present invention may be incorporated into any strut. Further, a plurality of radiopaque markers may be used with a stent, either on different struts or on a single strut. In one embodiment, eight radiopaque markers may be used in combination with a stent, with four markers being associated with four separate struts at a proximal end of the stent and four markers being associated with four separate struts at a distal end of the stent. This may be preferred to more clearly define the front and rear portions of the stent for improved positioning with respect to a target site of a body vessel.

The strut 12a and marker 18 of FIG. 1 are shown in greater detail in FIGS. 2 and 3. FIG. 3 shows the marker 18 separate from the strut 12a, as they would be prior to assembly. The marker 18 has an inner surface 22 adapted for engagement with the strut 12a. If the cross-section of the associated strut is generally circular, as in FIGS. 1-3, the inner surface preferably has an arcuate cross-section to mate with the strut. To increase the contact area between the marker and the strut, the inner surface may have an arcuate, generally C-shaped cross-section, as shown in FIGS. 1-3.

The shape of the inner surface may vary to more closely match the shape of the associated strut. For example, FIG. 4 illustrates a marker 18a having an inner surface 22a with a generally L-shaped cross-section to mate with a strut 16a having a generally rectangular cross-section. Other inner surface configurations, including a generally planar inner surface, may be employed without departing from the scope of the present invention.

In other embodiments, the inner surface may be adapted to provide a relatively tight fit with the associated strut, which may simplify the assembly and fixation processes, as well as encouraging long-term fixation of the marker to the strut. However, as described in greater detail herein, other means are provided for securing the marker to the strut, so a tight fit therebetween is not required.

The marker 18, 18a also includes an outer surface 24, which is spaced away from the inner surface 22, 22a by a thickness 26. In the illustrated embodiments, the thickness is substantially uniform, such that the cross-section of the marker mimics the cross-section of the inner surface. However, the thickness may vary, resulting in an outer surface having a different cross-section than the inner surface. The outer surface extends beyond the surface of the stent, so the shape of the outer surface may be selected to provide a number of functions, such as acting as an engagement surface for a delivery or deployment device. For example, U.S. Pat. No. 6,955,685, previously incorporated by reference hereinto, describes radiopaque markers providing an engagement function during delivery of a stent to a body vessel, and the outer surface of radiopaque markers according to the present invention may be adapted to provide a similar function.

The marker also includes at least one through-hole 28. The embodiment of FIGS. 1-3 is illustrated with two through-holes 28 (best shown in FIG. 3), while the embodiment of FIG. 4 is illustrated with one through-hole 28. Each through-hole 28 passes through the thickness 26 to allow for access to a portion of the strut 12a, 12b underlying the marker 18, 18a when the inner surface 22, 22a is engaged against the strut 12a, 12b. The through-holes 28 are illustrated as being generally circular, which may be preferred to simplify the manufacturing process, but other shapes may be used without departing from the scope of the present invention.

Each through-hole 28 is adapted to receive a weld 30 (FIG. 2) which secures the marker 18, 18a to the strut 12a, 12b. The weld 30 is applied through the through-hole 28, which is why the through-holes 28 must extend through the entire thickness 26 of the marker 18, 18a. Preferably, the through-hole 28 is sufficiently sized to fully receive the entire weld 30, because the weld may present an irregular and/or non-atraumatic surface if allowed to extend outside of the through-hole 28.

As the marker and strut are joined by a welding step, they should each be constructed from a material that is weldable to the material selected for the other structure, with the additional requirement that at least a part of the marker material is radiopaque. Suitable material for the strut/stent includes, but is not limited to, a stainless steel, nitinol material, and other material known for use in stent manufacture. If the stent is self-expanding, a material having shape memory properties, such as a nitinol material may be preferred. Suitable material for the marker is detectable under x-ray, fluoroscopy and the like, and includes, but is not limited to, platinum, gold, tantalum, zirconium and other materials having radiopaque properties.

Figure 5:
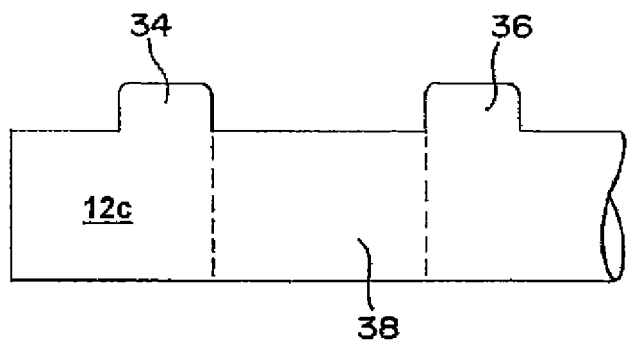
FIG. 5 is a front elevational view of a strut having a pair of projections according to an aspect of the present invention.
Figure 6:
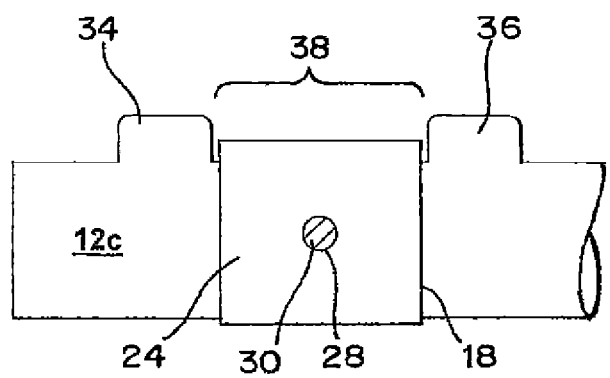
FIG. 6 is a front elevational view of the strut of FIG. 5 with a radiopaque marker.

Modifications may be made to the strut to further simplify the assembly process. For example, as shown in FIGS. 5 and 6, a strut 12c may be provided with one or more projections, such as a first projection 34 and a second projection 36. The projections may take any of a number of shapes, including an annular configuration extending along a perimeter of the strut 12c or a smaller post- or nipple-like structure extending radially away from the strut 12c. Other configurations may also be provided without departing from the scope of the present invention. Further, the shape of the first projection may differ from the shape of the second projection.

Each projection may be integrally formed with the strut, using whichever method is used to form the strut itself, or they may be applied during a separate step by shaping the strut or adding the projections as separate elements. Any other method of applying each projection may also be employed without departing from the scope of the present invention.

The projections, when a plurality are provided, are spaced apart from each other to define a receiving surface 38 of the strut 12c. The bounds of the illustrated receiving surface 38 are shown in FIG. 5 in broken lines. The receiving surface 38 is adapted to engage the inner surface of a radiopaque marker according to the present invention. Preferably, the distance between the projections is substantially equal to the length of the marker 18, as shown in FIG. 6, such that the marker 18 will be held against longitudinal movement along the strut 12c. This is particularly useful for holding the marker in place prior to or during the welding step.

In the illustrated embodiment, the height of each projection is greater than the thickness of the marker. However, the height of the projection or projections may be substantially equal to the thickness of the marker or even less than the thickness of the marker, provided that the projection or projections are at least configured to abut the end or ends of the marker to prevent movement along the strut.

In a method of securing a marker 18 to the strut 12c of FIGS. 5 and 6, the marker 18 is positioned between the projections and then the inner surface is positioned against the receiving surface 38. A weld 30 is then applied through each through-hole 28 to secure the marker 18 to the strut 12c.

A stent incorporating a radiopaque marker according to the present invention may be used according to any of a number of methods well-known to those of ordinary skill in the art. In one exemplary manner of use, the stent is inserted into the distal end of an introducer (not shown). The stent may be mounted about a guidewire or a balloon catheter before being inserted into the introducer.

When the stent has been properly loaded according to an introducer approach, the introducer is moved into the interior of a body vessel and positioned adjacent to a region of the vessel which is to be occluded. Thereafter, the stent is ejected from the introducer and into the target region. If the stent is not self-expanding, then a balloon is expanded to force the stent against the wall of the vessel. The markers assist in properly positioning the stent during deployment and in locating the stent after deployment.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An assembly implantable within a body vessel, the assembly comprising:
   a stent including a plurality of interconnecting struts defining a plurality of deformable cells allowing the stent to move between a compressed condition and an expanded condition, at least one of the struts having a free end portion with a receiving surface that has a first projection and a second projection, the first projection and the second projection each having a height that extends outwardly and away from the receiving surface, the receiving surface having a given size and shape;
   a radiopaque marker positioned over and assembled onto the receiving surface and adjacent to and between the first and second projections, the marker having an outer surface and an inner surface parallel to the outer surface and parallel to the receiving surface while engaging and closely matching in size and shape the receiving surface, the inner surface of the radiopaque marker is assembled onto the receiving surface and is parallel to and mates with the receiving surface, and the marker has a wall having a thickness, the wall thickness extending between the inner surface and the outer surface of the marker, said marker having an area with a width, length and uninterrupted perimeter defined by said width and length;
   said radiopaque marker further includes a through-hole fully contained within said marker uninterrupted perimeter and completely through said wall thickness of the marker, the through-hole having an inside surface;
   said assembly further includes a plug weld in a direction perpendicular to the receiving surface, said plug weld being within the through-hole and secured to the receiving surface underlying the radiopaque marker, the plug weld being engaged with and secured to both the through-hole inside surface and the receiving surface, whereby the marker is permanently secured to the receiving surface; and
   said length of the radiopaque marker is substantially equal to a distance between the first and second projections, with the receiving surface and the first and second projections cooperating to hold the marker against longitudinal movement along the free end portion of the stent.

2. The assembly of claim 1, wherein the marker and the plug weld comprise a discontinuous combination.

3. The assembly of claim 1, wherein the shape of the receiving surface is arcuate, and said inner surface of the marker that mates with the receiving surface has an arcuate cross-section.

4. The assembly of claim 1, wherein the shape of the receiving surface is C-shaped in cross-section, and said inner surface of the marker has a C-shaped cross-section and two free ends.

5. The assembly of claim 1, wherein the shape of the receiving surface is L-shaped in cross-section, and said inner surface of the marker has an L-shaped cross-section and two free ends.

6. The assembly of claim 1, wherein said thickness is substantially uniform and the receiving surface has a C-shaped cross-section, and said marker has a C-shaped cross-section and two free ends.

7. The assembly of claim 1, further comprising more than one through-hole.

8. A method of providing an assembly implantable within a body vessel, comprising:
   providing a stent having a plurality of interconnecting struts defining a plurality of deformable cells allowing the stent to move between a compressed condition and an expanded condition, at least one of the stent struts having a free end portion with a receiving surface that has a first projection and a second projection, the first projection and the second projection each having a height that extends outwardly and away from the receiving surface, the receiving surface having a given size and shape;

providing a radiopaque marker having a length substantially equal to a distance between the first and second projections, the marker having an outer surface and an inner surface parallel to the outer surface and parallel to the receiving surface and closely matching in size and shape the receiving surface, the marker further having a wall thickness extending between and separating the inner surface from the outer surface, the marker having an area with a width, length and uninterrupted perimeter defined by the width and length, and a through-hole passing through the thickness and fully contained within the marker uninterrupted perimeter, the through-hole having an inside surface;

positioning the inner surface of the marker against the stent such that the inner surface engages and closely matches the size and shape of the receiving surface;

assembling the inner surface of the radiopaque marker onto the receiving surface adjacent to and between the first and second projections and such that the through-hole allows for access to a portion of the at least one strut underlying the radiopaque marker; and welding the radiopaque marker to the at least one strut through the through-hole perpendicular to the receiving surface, thereby forming a plug weld that is fully received within the through-hole and secured to the receiving surface;

whereby the plug weld is permanently secured to the receiving surface, being engaged with and secured to both the through-hole inside surface and the receiving surface underlying the radiopaque marker, and the receiving surface and first and second projections cooperating to hold the marker against longitudinal movement along the free end portion of the stent.

9. The method of claim 8, wherein said providing a radiopaque marker includes providing a radiopaque marker having a plurality of through-holes and wherein said welding the radiopaque marker to the at least one strut includes welding the radiopaque marker to the at least one strut through each through-hole thereby forming a plurality of said plug welds.

* * * * *